United States Patent [19]
Hiraga et al.

[11] Patent Number: 4,582,937
[45] Date of Patent: Apr. 15, 1986

[54] PROCESS FOR RECOVERING ETHYLENEAMINES

[75] Inventors: Yoichi Hiraga; Tsugio Murakami, both of Shinnanyo; Hiroyuki Saito, Tokuyama; Osamu Fujii, Tokorozawa, all of Japan

[73] Assignee: Toyo Soda Manufacturing Co., Ltd., Shinnanyo, Japan

[21] Appl. No.: 722,422

[22] Filed: Apr. 12, 1985

Related U.S. Application Data

[63] Continuation of Ser. No. 500,361, Jun. 2, 1983, abandoned.

[30] Foreign Application Priority Data

Jun. 4, 1982 [JP] Japan ................................. 57-94952
Jul. 28, 1982 [JP] Japan ............................... 57-130482

[51] Int. Cl.$^4$ ............................................. C07C 85/26
[52] U.S. Cl. ................................... 564/498; 564/478; 564/482; 564/497; 564/511; 564/512; 544/358; 544/402
[58] Field of Search ............... 564/478, 482, 497, 498, 564/511, 512; 544/402, 358

[56] References Cited

U.S. PATENT DOCUMENTS 3,433,788 3/1969 Somekh et al. ..................... 564/497

FOREIGN PATENT DOCUMENTS 123287 6/1967 Czechoslovakia .
030805 3/1975 Japan ................................. 564/498

Primary Examiner—Charles F. Warren
Assistant Examiner—John A. Sopp
Attorney, Agent, or Firm—Oblon, Fisher, Spivak, McClelland & Maier

[57] ABSTRACT

Ethyleneamines are efficiently recovered from an aqueous solution thereof by extracting them from the aqueous solution into an organic phase with an extractant selected from carbonyl group-containing organic solvents, benzyl alcohol, carboxylic acids and salts thereof, alkylphosphoric acids and salts thereof, and mixed solvents containing at least one of these extractants. The ethyleneamines in the organic phase is recovered preferably from the organic phase to the aqueous phase by incorporating an acid therein, followed by phase separation.

18 Claims, No Drawings

PROCESS FOR RECOVERING ETHYLENEAMINES

This application is a continuation, of application Ser. No. 500,361, filed June 2, 1983, now abandoned.

BACKGROUND OF THE INVENTION (1) Field of the Invention

This invention relates to a process for recovering an ethyleneamine from an aqueous solution. More particularly, it relates to a process for the recovery of an ethyleneamine from an aqueous solution wherein the ethyleneamine is extracted from the aqueous solution by using an organic solvent, then recovered from the organic phase.

(2) Description of the Prior Art

The ethyleneamines to be recovered by the process of the present invention are not particularly limited and broadly include straight-chain and branched ethyleneamines such as ethylenediamine, diethylenetriamine, triethylenetetramine, tetraethylenepentamine, pentaethylenehexamine and tris-(2-aminoethyl)-amine, and cyclic ethyleneamines such as piperazine and N-aminoethylpiperazine. These ethyleneamines may be present alone or in combination in the aqueous solution to be treated by the process of the present invention.

These ethyleneamines are widely used as primary raw materials, secondary raw materials, and additives in various fields. For example, they are used as pesticides, paper strengthening agents, epoxy curing agents, and additives to lubricants, and in the production of polyamides.

These ethyleneamines are usually produced by the following two methods, although the ethyleneamines referred to in the present invention are not limited to those prepared by these methods.

(a) EDC Method

Ethylene dichloride (EDC) is reacted with ammonia at high temperature and pressure to form ethyleneamine hydrochlorides. These hydrochlorides are subjected to double decomposition with sodium hydroxide, and the sodium chloride by-product separated from the decomposition product.

(b) MEA Method

Monoethanolamine (MEA) is reacted with ammonia in the presence of a hydrogenation catalyst at high temperature and high pressure to obtain ethyleneamines.

In general, ethyleneamines produced by the reaction of ethylene dichloride and an aqueous ammonia are obtained as hydrochlorides in an aqueous mixed solution containing ammonium chloride. These ethyleneamines are usually recovered from the aqueous mixed solution by adding sodium hydroxide to the solution to effect double decomposition of the ethyleneamine hydrochlorides and ammonium chloride, heating to recover the liberated ammonia, and subsequently evaporating and concentrating the solution to recover the ethyleneamines while separating out the sodium chloride which crystallizes out.

This process has certain disadvantages.

For example, the reaction requires the use of a very large amount of water, all of which must be removed by evaporation; this entails a great expenditure of heat energy. Furthermore, the effective separation of sodium chloride from the ethyleneamines involves complicated operations and requires expensive apparatus for crystallization and separation.

One way to overcome these problems may be to effect extraction and separation using an organic solvent. However, ethyleneamines are extremely hydrophilic and hence difficult to transfer from the aqueous phase into the organic phase by an ordinary method. For this reason, one method for extraction using an organic solvent has been proposed in Japanese Examined Patent Publication No. 54-6523, whereby an aqueous solution containing ethyleneamines and incorporating 25 to 45% by weight of a sodium hydroxide is treated with a unipolar organic solvent to extract the ethyleneamines. This method still has a number of drawbacks. For example, a large excess of alkali must be added, in addition to which the aqueous phase must be re-used and the extraction carried at under special conditions.

SUMMARY OF THE INVENTION

It is a primary object of the present invention to provide a process for recovering ethyleneamines from an aqueous solution whereby the ethyleneamines can be recovered in high yield and in an advantageous manner.

Another object of the present invention is to provide a process for recovering ethyleneamines from an aqueous solution wherein the ethyleneamines are extracted into an organic phase in an enhanced percentage extraction.

Other objects and advantages of the present invention will be apparent from the following description.

In accordance with the present invention, there is provided a process for selectively recovering an ethyleneamine from an aqueous solution containing the ethyleneamine by transferring it into an organic phase, which comprises extracting the ethyleneamine from the aqueous solution with an extractant selected from the group consisting of carbonyl group-containing organic solvents, benzyl alcohol, carboxylic acids, alkylphosphoric acids and mixed organic solvents composed of at least one of these extractants and another organic solvent.

DESCRIPTION OF THE PREFERRED EMBODIMENTS

The ethyleneamine-containing aqueous solution to be treated with the extractant in the process of the present invention is not particularly limited. This may be a mixed liquid containing ethyleneamine hydrochlorides, ammonium chloride and free ammonia produced by the reaction between ethylene dichloride and aqueous ammonia, an aqueous solution obtained by adding an alkali such as calcium hydroxide or sodium hydroxide to said mixed liquid to alkalize the ethyleneamine hydrochlorides, or low-concentration aqueous solutions of amines produced in various processes. When an alkali is added to an aqueous solution containing an ethyleneamine prior to extraction with an organic extractant, ammonia is liberated. The liberated ammonia may either be removed from the solution prior to the extraction or remain present in the extraction step.

Of the extractants used in the process of the present invention, carbonyl group-containing organic solvents and benzyl alcohol are preferable because they extract ethyleneamines with enhanced selectivity and efficiency.

The term "carbonyl group-containing organic solvents" used herein refers to organic solvents having a ketone group and/or an aldehyde group. The ketone group-containing organic solvents may be either aliphatic or aromatic, although the former is preferable. Aliphatic ketone group-containing organic solvents include, for example, acyclic ketones preferably having 3 to 8 carbon atoms such as acetone, methyl ethyl ketone and methyl isobutyl ketone; and alicyclic ketones preferably having a 5- or 6-membered ring such as cyclopentanone, cyclohexanone and methylcyclohexanone. Of these, alicyclic ketones are most preferable. Aromatic ketone group-containing organic solvents include, for example, benzophenone.

The aldehyde group-containing organic solvents include, for example, aliphatic aldehydes preferably having 3 to 8 carbon atoms such as propionaldehyde and butylaldehyde, and aromatic aldehydes such as benzaldehyde.

The ketone group-containing organic solvents and the aldehyde group-containing organic solvents may be used either alone or in combination with other organic solvents. The organic solvents used in combination with the ketone group- or aldehyde group-containing organic solvents may be any organic solvent that does not react with the ketone or aldehyde group or with the ethyleneamines, and is capable of being mixed with the ketone group- or aldehyde group-containing organic solvent to form an organic phase separate from water. Such organic solvents include, for example, alcohols, ethers, and esters. Of these, alcohols are preferable in view of the extractability of the ethyleneamines. Alcohols having 3 to 8 carbon atoms are most preferable in view of their case of handling and phase separation, and their low cost.

Although the reasons why the ketone group- or aldehyde group-containing organic solvents are capable of selectively extracting ethyleneamines in high yield are not entirely clear, it is presumed that the ethyleneamines form adducts with the ketone group- or aldehyde group-containing organic solvents. Ethylenediamine and cyclohexanone, for instance, form an adduct such as

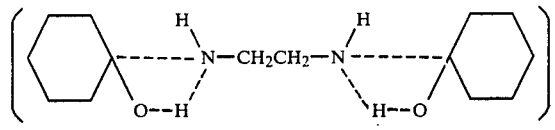

or interact in a manner somewhat similar to such a state, weakening the hydrophilic nature of the ethyleneamines such as to make them readily extractable into the organic phase.

Since the extraction of ethyleneamines is effected by the above type of adduct or interaction of the ketone group- or aldehyde group-containing organic solvent with the ethyleneamines, the use of the organic solvent in an amount of one mole or more per mole of the ethyleneamines is required in order to completely extract the ethyleneamines from the aqueous phase into the organic phase. This poses no problem when the ketone group- or aldehyde group-containing organic solvent is employed alone, since a considerable amount of the extracting solvent is required, owing to the above-described conditions, to separate the mixture into the two phases. However, when this solvent is employed in combination with other organic solvents, the ketone group- or aldehyde group-containing organic solvent should be present in an amount of one mole or more per mole of the ethyleneamines. The mixing ratio by volume of the ketone group- or aldehyde group-containing organic solvent to the other organic solvent is from 100:0 to 1:19, preferably from 100:0 to 1:9, and even more preferably from 100:0 to 1:4.

The extraction conditions and extracting apparatus are not particularly critical. Any extracting apparatus can be advantageously used at normal temperature under atmospheric pressure. The extraction method is also not particularly critical, but in order to recover ethyleneamines effectively at high efficiency, it is preferable to adopt the countercurrent multi-stage extraction method. When countercurrent multi-stage extraction is conducted using, for example, a 1:2 (by volume) mixed solvent of cyclohexanone and n-butanol as the extractant in a volume twice that of the aqueous ethyleneamine solution thereof, substantially the entire amount of the ethyleneamines in the aqueous solution can be recovered in the organic phase after only several stages. At that point, the percentage extraction of sodium chloride is only 1.5%, and even this sodium chloride can be completely separated out by washing the organic phase with an extremely small amount of water.

It is preferable to conduct the extraction by using a ketone group-containing organic solvent as an extractant in the presence of ammonia. This is because the presence of ammonia enables more effective and efficient recovery of the ethyleneamines irrespective of the type of aqueous ethyleneamine solution, as compared with the case in which no ammonia is present. This is particularly so when the aqueous ethyleneamine solution to be treated is either a solution containing both ethyleneamines and calcium chloride or a solution containing ethyleneamine hydrochlorides.

The extraction of ethyleneamines from the above-mentioned two types of solutions in the presence of ammonia will be described below following.

If a ketone group-containing solvent is employed as an extractant, it selectively extracts the ethyleneamines into the organic phase, thereby permitting the separation thereof from calcium chloride. However, when an attempt is made to extract further ethyleneamines from a residue containing a minor portion of the ethylenediamines and substantially all of the calcium chloride left after extraction of the ethylenediamines, the extractability of the ethyleneamines into the organic phase is greatly reduced. However, the presence of the ammonia not only minimizes this reduction in extractability due to a low ratio of ethyleneamines to calcium chloride, but has the further advantage of enhancing the extractability of the ethyleneamines as compared with the case where no ammonia is present.

Although the reason for the advantageous effect of the ammonia is not clear, it is presumed to be as follows. Each $Ca^{2+}$ ion in the aqueous phase is coordinated with water as shown in the following formula:

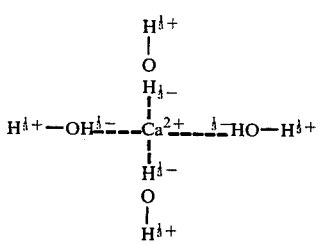

to form an aqua ion behaving as a weak acid. The extractability of the ethyleneamines into the organic phase is reduced by the interaction of this aqua ion with the ethyleneamines. However, if ammonia is present, the acid-like behavior of the aqua ion is neutralized by the ammonia, eliminating the above-described interaction, and thereby improving the extractability of the ethyleneamines.

With certain exceptions, no special treatment is needed to include ammonia in the extraction system. The reason for this is that, since the reaction between ethylene dichloride and an aqueous ammonia is usually carried out in the presence of a large stoichiometric excess of ammonia, a large amount of ammonia is present in the reaction mixture. Therefore, it is only necessary to add calcium hydroxide to the reaction mixture to effect the double decomposition of the ethyleneamine hydrochlorides and ammonium chloride, then extract the ethyleneamines. The amount of the ammonia present should be at least 2.0 moles, and preferably at least 6.0 moles, per mole of the $Ca^{2+}$ ions present. Moreover, since the extractability of the ammonia into the organic phase is extremely low, there is no need whatsoever to control the amount of the ammonia present during the extraction step.

As hereinbefore mentioned, the extraction conditions and extracting apparatus are not particularly critical. Any extracting apparatus can be advantageously used at normal temperature under atmospheric pressure. The extraction method is not particularly critical, but in order to recover ethyleneamines effectively at high efficiency, it is preferable to adopt the countercurrent multi-stage extraction method. For example, when this counter-current multi-stage extraction is conducted using a 1:2 (by volume) mixed solvent of cyclohexanone and n-butanol as the extractant in twice the volume of that of the ethyleneamines present in the aqueous solution thereof, substantially all of the ethyleneamines in the aqueous solution can be recovered in the organic phase after only by several stages. At this point, the percentage extraction of calcium chloride is only 5 to 6%, and even this calcium chloride can be completely separated out by washing the organic phase with an extremely small amount of water. In some cases, a minor amount of ammonia remains in the organic phase. This ammonia can easily be removed by distilling the organic phase, if desired.

Furthermore, if a ketone group-containing solvent or a mixture thereof with another solvent is used in the presence of ammonia for the extraction of ethyleneamines from a solution containing ethyleneamine hydrochlorides, the extractability of ethyleneamines is enhanced. Although the reason for such an advantageous effect is not clear, this is presumed to be as follows.

In an aqueous solution containing ethyleneamines, ammonia and hydrochloric acid, since the $PK_a$ values are higher for the ethyleneamines than for the ammonia, most of the hydrochloric acid is present as ethyleneamine hydrochlorides rather than as ammonium chloride. However, since an equilibrium relationship exists in the liquid, part of the ethyleneamines are present in the free form. In the case of ethylenediamine, for example, the following relationship is believed to exist:

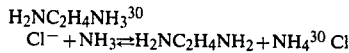

When an aqueous solution having this type of equilibrium relationship is subjected to the action of a ketone group-containing solvent, the free ethyleneamines and the alicyclic ketone form adducts. For example, in the case of ethylenediamine and cyclohexanone, the following adduct

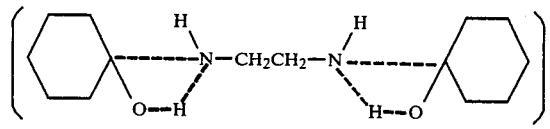

or a similar interaction is formed, weakening the hydrophilic nature of the ethyleneamines, and enabling the ethyleneamines to be extremely efficiently extracted into the organic phase. As a result, the above equilibrium equation proceeds in the right-hand direction, enabling the ethyleneamines and hydrochloric acid to be efficiently separated.

As is clear from the above description, the amounts of the ketone group-containing solvent and ammonia used are as follows. The ketone group-containing solvent should be used in an amount of at least one mole per mole of the ethyleneamines; i.e., in at least a stoichiometric amount for the interaction between one amino group of the ethyleneamines and the ketone group-containing solvent. Since ammonia does not form an adduct with the ketone group-containing solvent, one mole or more per mole of the hydrochloric acid present is sufficient. The ketone group-containing solvent should preferably be used in an amount of at least 2 moles per mole of the ethyleneamines to provide more efficient extraction of the ethyleneamines.

With the exception of certain cases, no special treatment is needed to include ammonia in the extraction system for the following reason. The reaction of ethylene dichloride and an aqueous ammonia is usually carried out in the presence of a large stoichiometric excess of ammonia. Thus, a large amount of ammonia is present compared with the amount of the ethyleneamine hydrochlorides in the reaction mixture, enabling this to be supplied directly to the ethyleneamine extraction step. Furthermore, since the distribution of ammonia in the organic phase is small compared with the ethyleneamines, no control whatsoever is needed over the amount of ammonia present in the extracting step.

The extraction conditions and extracting apparatus are not particularly critical. Any extracting apparatus can be advantageously used at normal temperature under atmospheric pressure. The extraction method is not particularly critical, but in order to recover ethyleneamines effectively at a high efficiency, it is preferable to adopt the countercurrent multi-stage extraction method. For example, when countercurrent multi-stage extraction is conducted on an aqueous reaction mixture produced from ethylene dichloride and an aqueous ammonia using a 1:2 (by volume) mixed solvent of cyclohexanone and n-butanol as the extractant in a volume twice that of the aqueous ethyleneamine solution, substantially all of the ethyleneamines in the aqueous solution can be extracted into the organic phase within 2 to 4 stages. At this point the percentage extraction of ammonium chloride by-product obtained by the extraction of the ethyleneamines contained in this reaction mixture may be as low as 5%; in addition, this co-extracted ammonium chloride can easily be removed by washing the organic phase with a small amount of water, thereby completely separating the ethyleneamines and the chloride ions. In some cases, a minor amount of ammonia remains in the organic phase. If desired, this ammonia can easily be removed by distilling the organic phase.

Ethyleneamines can also be extracted into the organic phase efficiently when benzyl alcohol is used. The reasons why ethyleneamines can be extracted at high efficiency with benzyl alcohol are not entirely clear. However, in view of the properties of ethyleneamines, it is thought that the amino groups of the ethyleneamines are inactivated by the formation of adducts through the reaction of benzyl alcohol with the amino groups of the ethyleneamines or through the influence of benzyl alcohol on the amino groups of the ethyleniamines, resulting in the loss of its hydrophilic properties attributable to the amino groups, and causing the ethyleneamines to become organophilic.

The manner in which the benzyl alcohol is used is not particularly critical. The amount of benzyl alcohol necessary for rendering ethyleneamines organophilic differs to some extent according to the composition of the ethyleneamines, but benzyl alcohol is ordinarily used in an amount of at least 0.3 mole, and preferably at least 0.5 mole, per mole of the amino groups of the ethyleneamines. The solvent used for formation of the organic phase and extraction of ethleneamines is not limited to benzyl alcohol only, but may consist of mixtures of benzyl alcohol with various organic solvents. Any organic solvents capable of forming an organic phase and unreactive with benzyl alcohol may be used. When such factors as the extraction and phase-separation properties, ease of handling, and cost are taken into account, the use of aliphatic alcohols having 3 to 8 carbon atoms is preferred. For example, a mixture of benzyl alcohol and n-butanol or a mixture of benzyl alcohol and isoamyl alcohol are advantageously used. The content of benzyl alcohol in these mixed solvents ordinarily ranges from 5 to 80% by volume.

Since ethyleneamines are in the free state in the aqueous solution obtained by treating the reaction mixture of ethylene dichloride and aqueous ammonia with sodium hydroxide or calcium hydroxide, the ethyleneamines extracted in the organic phase are naturally in the free state. Furthermore, the ethyleneamines extracted from a mixed aqueous solution of the reaction products, that is, ethylene amine monohydrochlorides, ammonia and ammonium chloride, are in the free state. The reason for this is not entirely clear, but it appears that the interaction between benzyl alcohol and the amino groups in the ethylene amine hydrochlorides that have not combined with the hydrochloric acid, reduces the alkalinity below that of ammonia, resulting in dehydrochlorination by the ammonia and the extraction of free ethyleneamines. One of the characteristic features of the present invention is that the ethyleneamines are separated selectively without resorting to caustic treatment.

When benzyl alcohol is used, the extractability of ethyleneamines, expressed in terms of the distribution coefficient, i.e., the organic phase/aqueous phase concentration ratio, is a minimum of 0.5, and ordinarily ranges from 1 to 3, although this value varies to some extent according to the type of inorganic chloride present in the system, the concentration of the ethyleneamines, and the ratio of the ethyleneamines to the inorganic chloride. The type of inorganic chloride has the greatest influence on this distribution coefficient. When calcium chloride is present, the extractability of the ethyleneamines is inferior to the extractability attained when other salts are present. The reason for this is thought to be that water combines with $Ca^{2+}$ ion to form an aqua ion that acts as a weak acid; the interaction between this aqua ion and the ethyleneamines, which act as bases, reduces the extractability of the ethyleneamines into the organic phase. Accordingly, in the calcium chloride-present system, in order to eliminate the influences of the aqua ion, ammonia is made co-present, thereby increasing the extractability to 2 to 6 times that when ammonia is not present. Therefore, the extraction should presently be carried out without the removal of ammonia from the liquid formed by the caustic treatment with calcium hydroxide.

In order to further improve the ethyleneamine-extractability, it is desirable that an organic solvent containing a ketone group, such as acetone, methylethyl ketone, cyclohexanone or cyclopentanone be used in combination with benzyl alcohol. When this mixed solvent is used, the extractability of ethyleneamines is improved over the extractability attained when benzyl alcohol or the ketone group-containing organic solvent is used alone, although the reason for this is not known.

According to the process of the present invention, ethylenediamines can be extracted very efficiently, as pointed out hereinbefore. Thus, for example, if countercurrent multi-stage extraction is carried out in 3 to 10 extraction stages by using the extractant in an amount of 2 to 10 parts by volume per part by volume of the starting aqueous solution, substantially all ethyleneamines contained in the starting aqueous solution can be extracted. The distribution coefficient of the chloride present in the initial aqueous solution is very small, being at most 0.1 and ordinarily smaller than 0.02; the amount of the chloride extracted together with ethyleneamines into the organic phase is therefore very small. The chloride co-extracted in the organic phase can simply be removed from the organic phase merely by contacting the extracted phase with a small amount of water or a small amount of an aqueous solution of ethyleneamines.

Also, when a carboxylic acid or an alkyl phosphate is used, ethylene amines can be extracted into the organic phase efficiently. The reason for this will now be described with reference to carboxylic acids.

In the following reaction:

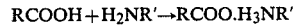

the amino groups in the ethyleneamines, which are highly hydrophilic, are inactivated and the high-molecular-weight hydrocarbon of the organophilic group is bonded to these amino groups, making the ethyleneamines organophilic.

The carboxylic acid or alkylphosphoric acid used in the present invention is organophilic and highly soluble in organic solvents. Any carboxylic acids and alkylphosphoric acids having limited water solubility may be used. For example, these may be carboxylic acids used as extractants, including carboxylic acids having 6 to 20 carbon atoms, and preferably 9 to 20 carbon atoms. More specifically, these may be naphthenic acid, pelargonic acid and tertiary fatty acids represented by the following general formula:

$$(CH_3)(R_1)(R_2)CCOOH$$

wherein $R_1$ and $R_2$, which may or may not be the same, stand for alkyl groups having 1 to 8 carbon atoms, and marketed under the tradename, Versatic Acid, by Shell Chemical.

Alkylphosphoric acids customarily used as extractants may be used, as in case of the carboxylic acid. For example, monoalkyl- and dialkylphosphoric acid can be used. As the monoalkylphosphoric acid, those containing an alkyl group having 4 to 20 carbon atoms, such as mono-n-octyl phosphate, mono-2-ethylhexylphosphoric acid, and mono-2,6,8-trimethylnonyl-4-phosphoric acid may be cited. As the dialkyl phosphate, those containing alkyl groups having 8 to 30 carbon atoms, such as di-n-octylphosphoric acid, di-2-ethylhexylphosphoric acid, and dioctylphenylphosphoric acid may be cited. In view of the availability, price and ease of handling, naphthenic acid or Versatic Acid is preferable as the carboxylic acid, and a dialkylphosphoric acid such as di-2-ethylhexylphosphoric acid (D-2-EHPA) is preferable as the alkylphosphoric acid. Both the carboxylic acid and alkylphosphoric acid may be used in the form of a salt, such as a sodium or calcium salt.

Ethyleneamines bonded to the above-mentioned carboxylic acid or alkylphosphoric acid are very organophilic, and can therefore easily be extracted from the aqueous phase with an ordinary organic solvent, e.g., an alcohol such as butanol or pentanol, a ketone such as methyl ethyl ketone or methyl isobutyl ketone, or an aromatic hydrocarbon such as benzene or toluene.

Accordingly, in carrying out the process of the present invention, it is preferable in practice that a mixed solvent formed by dissolving the carboxylic acid or alkylphosphoric acid in an ordinary organic solvent such as those mentioned above be used as the solvent for extracting ethyleneamines. The concentration of the carboxylic acid or alkylphosphoric acid in the mixed solvent is ordinarily from 0.1 to 3 mole/l, with a concentration of from 0.5 to 1.0 mole/l preferable from the standpoint of the phase-separation properties.

When the carboxylic acid or alkylphosphoric acid is used in the form of a salt such as a sodium salt or calcium salt, it is preferable to use these compounds for the extraction of ethyleneamines from an aqueous solution containing the ethyleneamines in a combined state; that is, in the form of, ethyleneamine monohydrochlorides, for example, because this provides a better extractability.

Since ethyleneamines are extracted in the organic phase in the form of adducts to the carboxylic acid or alkylphosphoric acid, it is necessary that the carboxylic acid or alkylphosphoric acid be used in an amount of at least 1 mole, preferably at least 2 moles, per mole of the ethyleneamines. Since the concentration of ethyleneamines in the aqueous reaction mixture prepared from ethylene dichloride and aqueous ammonia is ordinarily 1 to 2 mole/l, use of the extractant in an amount 2 to 8 times (by volume) the amount of the aqueous solution is sufficient. Any extracting apparatus and extraction method may be adopted at normal temperature under atmospheric pressure. Countercurrent multi-stage extraction is preferred because this provides highly efficient extraction of ethyleneamines. For example, when 5 parts by volume of an n-butanol solution containing 1 mole/l of the carboxylic acid or alkylphosphoric acid is brought into countercurrent contact with 1 part by volume of an aqueous solution containing 1.5 mole/l of ethyleneamines, the ethyleneamines can be recovered at a ratio higher than 99% after 5 to 10 stages.

Only a very slight amount of the chloride is contained in the extracted phase thus obtained, and this chloride can easily be removed from the organic phase into the aqueous phase by contacting the extracted phase with a small amount of water. In this operation, no ethyleneamines is transferred into the aqueous phase.

As is apparent from the foregoing description, ethyleneamines are selectively extracted with specific organic solvents. Various methods may be adopted for recovering ethyleneamines from the organic solvent phase.

More specifically, when an organic solvent having a ketone or aldehyde group is used, ethyleneamines can be recovered by distillation, which depends upon the particular type of solvent.

When benzyl alcohol is used, a method may be employed in which the extracted phase is contacted with pure water to back-extract the ethyleneamines, and the ethyleneamines recovered in the form of an aqueous solution. Another possible method is one whereby the organic phase is subjected to distillation to recover the ethyleneamines.

When a carboxylic acid or an alkylphosphoric acid is used as the solvent, ethyleneamines are recovered by using an alkali. Sodium hydroxide, potassium hydroxide, calcium hydroxide and magnesium hydroxide may be used as the alkali. Of these, sodium hydroxide or calcium hydroxide is preferred.

However, special care is warranted when carboxylic acid and sodium hydroxide are used, because the resulting sodium salt of the carboxylic acid has a high surfactant potential, causing the formation a homogeneous phase under certain conditions, rather than the formation of an aqueous solution containing ethyleneamines. In order to prevent the formation of this homogeneous phase, the concentration and amount of the aqueous solution of sodium hydroxide to be used in the recovery step should be controlled so that the concentration of sodium hydroxide in the aqueous phase to be formed is at least 10%, and preferably, at least 15% by weight.

The organic solvent phase containing the salt of the carboxylic acid or alkylphosphoric acid, which forms during the recovery step, is recycled directly to the ethyleneamine extraction step, or the organic solvent phase treated with sulfuric acid or hydrochloric acid to revert the salt of the carboxylic acid or alkylphosphoric acid back to its carboxylic acid or alkylphosphoric acid and then recycled to the ethyleneamine extraction step.

The recovery of ethyleneamines from the above-mentioned organic phase should preferably employ a method in which the ethyleneamines are converted to the salts using an acid and the salts transferred from the organic phase into the aqueous phase. This method is very efficient when the intended end products are ethyleneamine salts. However, if free ethyleneamines are desired (this case is generally more common), the recovered ethyleneamine salts must be alkalized with an alkali such as sodium hydroxide and calcium hydroxide and the by-product salt, e.g., sodium salts and calcium salts, removed from the alkalized reaction mixture.

There is no particular restriction on the acid used for the back-extraction of ethyleneamines, i.e., for the recovery of ethyleneamines from the organic phase, and either inorganic or organic acid may usually be employed. However, inorganic acids, including, for example, hydrochloric acid, sulfuric acid, carbonic acid or carbon dioxide, hydrofluoric acid and nitric acid are preferred. When ethyleneamines are intended as the final products, sulfuric acid and carbonic acid or carbon dioxide are preferable over hydrochloric acid, nitric acid, and hydrofluoric acid, because hydrochloric acid and nitric acid do not form water-insoluble salts, while hydrofluoric acid is expensive and highly corrosive. The amount of the acid used may be such that at least one amino group in the ethyleneamine molecules can be converted into a salt. Monobasic acids such as hydrochloric acid, nitric acid, or hydrofluoric acid are normally used in an amount of 1 to 2 moles, while dibasic acids such as sulfuric acid and carbonic acid or carbon dioxide are used in an amount of 0.5 to 1 mole, per mole of ethyleneamines. Although the use of the acid in an amount exceeding the above does not interfere with back-extraction, this is not desirable when ethyleneamines are desired, because the amount of the acid to be removed is increased. However, carbonic acid and carbon dioxide may be used in an excessive amount because these compounds are volatile and can easily be removed. This back-extraction is extremely efficient because the ethyleneamines are back extracted into the aqueous phase as salts insoluble in the organic phase. In general, the concentration of ethyleneamines can be increased at least five-fold as compared with before extraction. As much as 80% or more of the water, heretofore removed by evaporation, may be removed instead by back-extraction without the use of heat energy.

The method for the recovery of ethyleneamines from the aqueous solution of high concentrations of ethyleneamine salts thus prepared is not particularly restricted, and various methods may be adopted. For example, one such method is that in which sodium hydroxide or calcium hydroxide is added to the aqueous solution to crystallize out and separate off sodium chloride, calcium sulfate, or calcium carbonate. In this case, the concentration of ethyleneamines is high, reducing the solubility of the salts to be produced. Furthermore, since salts having low solubility are produced, the complex operations and apparatus employed in conventionally concentration-crystallization procedures are not required at all. Moreover, a method in which an aqueous solution of ethyleneamine salts is brought into contact with an anion exchange resin or an anion exchange liquid is advantageous in some cases.

If the organic phase from which ethyleneamines are back-extracted using an acid comprises a ketone group-containing organic solvent or benzyl alcohol, the back-extraction can be performed very efficiently. Even if the acid used is a weak acid such as carbonic acid or carbon dioxide, back-extraction can be carried out very easily and efficiently.

An aqueous carbonic acid solution or carbon doxide are optimum ideal as the acids. Since the ethylene amines are recovered from the organic phase in the form of salts, if acids other than carbonic acid and carbon dioxide are used, the ethyleneamine salts must be alkalized by adding an alkali, and the by-product salts removed to obtain free ethyleneamines. On the other hand, if an aqueous carbonic acid solution or carbon dioxide is used, free ethyleneamines can easily be recovered without alkalization of the ethyleneamine salts. This is because the ethyleneamine carbonates are thermally unstable, when heated, they undergo decomposition, as shown in the following formula, resulting in dissipation of the carbon dioxide, allowing free ethyleneamines to be easily recovered.

$$(CH_2NH_2)_2H_2CO_3 \rightarrow (CH_2NH_2)_2 + CO_2 \uparrow + H_2O$$

In the back-extraction step in which the ethyleneamine-containing organic phase is brought into contact with carbon dioxide or an aqueous carbonic acid solution, the reaction for the formation of ethyleneamine carbonates proceeds very rapidly, presenting no special problems in practice. However, if the organic phase is brought into direct contact with carbon dioxide, extremely fine ethyleneamine carbonate crystals form; this increases the viscosity, leading to reduced contact with carbon dioxide. Therefore, it is preferable to contact the organic phase with carbon dioxide in the presence of water and recover the ethyleneamines as an aqueous carbonate solution. While there is no particular restriction on the method of contacting, one method that can be used advantageously is an air lift method whereby the ethyleneamine-containing solvent phase, water, and carbon dioxide are simultaneously supplied to a contact-treating zone; another preferred method involves the mixture with the organic phase of an aqueous carbonic acid solution prepared by dissolving carbon dioxide in water under pressure.

After the completion of the reaction, the mixed liquid is left standing, and allowed to separate into an aqueous phase and a solvent phase. Since the ethyleneamine carbonates are substantially insoluble in the organic phase, they are substantially all recovered in the aqueous solution. The concentration of the ethyleneamines in the aqueous solution are at least 200 g/l, but vary somewhat depending on the amount of water used. The separated organic phase is recycled for reuse as the ethyleneamine-extracting solvent, and the aqueous phase transferred to the decarbonation step.

The carbon dioxide gas used in the back-extraction step may range from product having a concentration of almost 100% and obtained as a by-product in petrochemical industry, to with a concentration of 40% obtained from a lime kiln. However, since the majority of the carbon dioxide used in the back-extraction step is generally derived from the 100% carbon dioxide gas generated in the decarbonation step, the carbon dioxide gas used in the back-extraction step may be of high concentration even though the carbon dioxide gas supplied from outside the system is dilute. In addition, the amount of carbon dioxide consumed is minor, making it possible to carry out the process of this invention can even in the absence of a carbon dioxide source such as a lime kiln.

The aqueous ethyleneamine carbonate solution obtained from the organic phase is then heated in the decarbonation step; the ethyleneamine carbonates are readily decomposed to generate carbon dioxide, giving free ethyleneamines. This process makes it possible for all the carbon dioxide gas used in the back-extraction step to be of high concentration. Since decarbonation can be achieved merely by heating the aqueous ethyleneamine carbonate solution at normal pressure, no special apparatus or operation is needed. The thermal decomposition temperature is generally from 60° to 120° C., and preferably from 80° to 120° C. The degree of decarbonation may vary to some extent depending on the concentrations of ethyleneamine carbonates supplied, the treatment temperature, and the reaction time. For example, under decomposition conditions where the aqueous ethyleneamine carbonate solution is heated at the boiling point for one hour, 90% or more of the carbon dioxide gas supplied can be removed at a concentration of ethyleneamines of 200 g/l, and 80% or more thereof can be removed at a concentration of 300 g/l. Furthermore, when an organic solvent such as butyl alcohol is present in the aqueous solution, the degree of decarbonation is even more enhanced, and substantially all of the carbon dioxide can be removed.

As described above, the combined use of a solvent having reactivity with ethyleneamines and a solvent such as butyl alcohol is possible in this invention; moreover, because butyl alcohol has some solubility in water, the aqueous ethyleneamine carbonate solution obtained in the back-extraction step generally contains a minor amount of butyl alcohol. The presence of butyl alcohol facilitates the removal of carbon dioxide in the decarbonation step.

The aqueous solution of free ethyleneamines thus obtained usually contains 200 g/l or more of ethyleneamines. If small amounts of the ethyleneamine carbonates are still contained in this aqueous solution, they may be removed as sodium carbonate, calcium carbonate, etc., by adding a small amount of sodium hydroxide, calcium hydroxide or the like. When sodium hydroxide is employed, two phases, i.e., an aqueous sodium carbonate phase and an ethyleneamine phase, are formed; it is therefore preferable here to use sodium hydroxide. Since the aqueous solution obtained in the recovery step contains ethyleneamines at a concentration of 300 g/l or more and is almost free of components other than the ethyleneamines and water, it is possible to easily obtain various ethyleneamines by a conventional distillation operation.

The advantages of the method of this invention may be summarized as follows:

(1) Ethyleneamines can be concentrated by a highly energy efficient operation. This is in a striking contrast to the conventional procedure in which the concentration of ethyleneamines achieved is about 100 g/l, and it is necessary to remove an amount of water of about 6 times by weight that of the ethyleneamines in order to raise the concentration to 300 g/l.

(2) Since the separation of chloride ions can be achieved by an extraction method, there is no need for the use of costly sodium hydroxide, and inexpensive calcium hydroxide may be employed.

(3) If carbon dioxide gas or an aqueous carbonic acid solution is used in the back extraction step, free ethyleneamines can easily be recovered without the use of an alkali for the decomposition of the ethyleneamine salts.

(4) The special apparatus and operations required in conventional processes, such as the crystallization and separation of sodium chloride, are not necessary.

(5) The product obtained is of a high purity.

The present invention will now be described in detail by the following examples. These examples by no means limit the scope of the present invention.

In the examples, percents are given by weight unless otherwise specified.

EXAMPLES 1 THROUGH 5

To 100 ml of an aqueous solution containing 8.0 g of ethylenediamine (EDA) and 15.0 g of sodium chloride (NaCl) was added an equal volume of a mixed solvent of cyclohexanone and n-butanol, the mixing ratio being as set forth in table I. Each mixture was shaken for 10 minutes, then allowed to stand to effect phase separation. The results of analysis are shown in Table I.

TABLE I

| Example No. | Extractant composition (vol. %) | | Extraction equilibrium composition | | | | % Extraction | |
|---|---|---|---|---|---|---|---|---|
| | | | EDA (g/l) | | NaCl (g/l) | | | |
| | Cyclohexanone | n-Butanol | Org. phase | Aq. phase | Org. phase | Aq. phase | EDA (%) | NaCl (%) |
| 1 | 100 | 0 | 49.4 | 33.0 | 1.3 | 129 | 52.5 | 0.7 |
| 2 | 33 | 67 | 54.6 | 18.6 | 1.8 | 183 | 81.2 | 1.4 |
| 3 | 20 | 80 | 55.3 | 19.7 | 1.8 | 172 | 78.8 | 1.4 |
| 4 | 10 | 90 | 48.1 | 30.1 | 2.0 | 164 | 66.1 | 1.5 |
| Comp. Ex. 1 | 0 | 100 | 14.3 | 68.9 | 2.6 | 157 | 18.9 | 1.6 |

Extractant ratio (extractant/aqueous EDA solution) = 1/1 by volume

EXAMPLES 5 THROUGH 8

To 100 ml of an aqueous solution containing 90 g/l of ethylenediamine (EDA), 150 g/l of calcium chloride (CaCl$_2$), and 140 g/l of ammonia (NH$_3$) was added an equal amount of an extractant. As the extractant, cyclohexanone and a 1:2 (by volume) mixed solvent of cyclohexanone (CH) and n-butanol (Bu) were separately used. Each mixture was shaken for 10 minutes, then allowed to stand to effect phase separation.

The above-mentioned procedures were repeated without the addition of ammonia, all other conditions remaining substantially the same.

The results are shown in Table II.

TABLE II

| Example No. | Extractant | NH$_3$ | Extraction equilibrium composition | | | | | | % Extraction | | |
|---|---|---|---|---|---|---|---|---|---|---|---|
| | | | EDA (g/l) | | NH$_3$ (g/l) | | CaCl$_2$ (g/l) | | | | |
| | | | Org. phase | Aq. phase | Org. phase | Aq. phase | Org. phase | Aq. phase | EDA | NH$_3$ | CaCl$_2$ |
| 5 | Cyclohexanone (CH) | Absent | 25.3 | 54.5 | — | — | 0.3 | 111.0 | 18.3 | — | 0.13 |
| 6 | CH/Bu = ½ | Absent | 51.0 | 39.0 | — | — | 7.8 | 153.9 | 62.0 | — | 5.6 |

TABLE II-continued

| | | | Extraction equilibrium composition | | | | | | | | |
|---|---|---|---|---|---|---|---|---|---|---|---|
| | | | EDA (g/l) | | NH₃ (g/l) | | CaCl₂ (g/l) | | % Extraction | | |
| Example No. | Extractant | NH₃ | Org. phase | Aq. phase | Org. phase | Aq. phase | Org. phase | Aq. phase | EDA | NH₃ | CaCl₂ |
| 7 | Cyclo-hexanone (CH) | Present | 40.2 | 47.8 | 3.1 | 136.9 | 0.0 | 118.0 | 32.6 | 2.2 | 0.0 |
| 8 | CH/Bu = ½ | Present | 62.7 | 21.1 | 14.1 | 145.6 | 6.6 | 167.5 | 80.1 | 11.6 | 5.1 |

EXAMPLE 9

To 100 ml of an aqueous solution containing 90 g/l of ethylenediamine, 150 g/l of CaCl₂ and 40 g/l of NH₃ was added 100 ml of a 1:2 (by volume) mixed solvent of cyclohexanone and n-butanol. The mixture was shaken for 10 minutes, then allowed to stand to effect separation into aqueous and organic phases. This gave 110 ml of an organic phase containing 56.2 g/l of ethylenediamine, which means the percentage extraction of ethylenediamine was 68.8%.

EXAMPLE 10

A 50% calcium hydroxide cake was added to an aqueous reaction mixture obtained by the reaction of ethylene dichloride (EDC) and an aqueous ammonia, giving an aqueous solution containing 65 g/l of ethylenediamine (EDA), 28 g/l of diethylenetriamine (DETA), 16 g/l of triethylenetetramine (TETA), 6.0 g/l of tetraethylenepentamine (TEPA), 4.0 g/l of pentaethylenehexamine (PEHA), 4.0 g/l of N-aminoethlpiperazine (N-AEP), 176 g/l of CaCl₂ and 108 g/l of NH₃. To 100 ml of the aqueous solution was added 100 ml of a mixed solvent of n-butanol containing 33 ml of cyclohexanone. The mixture was shaken for 10 minutes, then allowed to stand to effect phase separation. This gave 115 ml of an organic phase containing 45 g/l of EDA, 17 g/l of DETA, 9.3 g/l of TETA, 3.2 g/l of TEPA, 2.0 g/l of PEHA and 1.8 g/l of N-AEP was obtained, which means that the percentage extraction was 80% for EDA, 71% for DETA, 67% for TETA, 62% for TEPA, 58% for PEHA, and 52% for N-AEP.

EXAMPLE 11

A 50% calcium hydroxide cake was added to an aqueous solution obtained by reaction between ethylene dichloride and an aqueous ammonia to obtain 200 ml of an aqueous solution containing 65 g/l of ethylenediamine (EDA), 28 g/l of diethylenetriamine (DETA), 16 g/l of triethylenetetramine (TETA), 6.0 g/l of tetraethylenepentamine (TEPA), 4.0 g/l of pentaethylenehexamine (PEHA), 4.0 g/l of N-aminoethylpiperazine (N-AEP), 176 g/l of CaCl₂ and 108 g/l of NH₃.

To this solution was added 200 ml of a mixed solvent of cyclohexanone containing 133 ml of benzyl alcohol. The mixture was shaken for 10 minutes, then allowed to stand to effect phase separation.

This gave 240 ml of an organic phase containing 47.2 g/l of EDA, 18.4 g/l of DETA, 10.5 g/l of TETA, 3.8 g/l of TEPA, 2.5 g/l of PEHA, and 2.2 g/l of N-AEP.

EXAMPLE 12

To 200 ml of an aqueous solution containing 145 g/l of ethylenediamine (EDA) monohydrochloride was added 300 ml of a 1 m solution of di-2-ethylhexylphosphoric acid in n-butanol. The mixture was shaken for 10 minutes, then allowed to stand to effect phase separation. This gave 318 ml of an organic phase containing 28.3 g/l of EDA.

To 150 ml of the organic phase so obtained was added 10 ml of an aqueous sodium hydroxide solution at a 600 g/l concentration. The mixture was shaken for 10 minutes, and then allowed to stand to effect phase separation, giving 14 ml of an aqueous phase containing 300 g/l of EDA.

EXAMPLE 13

Three-stage counter-current extraction was carried out on an aqueous solution containing 90 g/l of ethylenediamine (EDA) and 150 g/l of sodium chloride using a 1:2 (by volume) mixed solvent of cyclohexanone and n-butanol in a volume twice that of the aqueous solution.

The resulting percentage extraction of EDA in the organic phase was 99%, and the percentage extraction of sodium chloride, 1.5%.

To 100 ml of the organic phase containing EDA extracted therein was added 10 ml of water. The mixture was shaken for 10 minutes, then allowed to stand to effect phase separation. No sodium chloride was found in the organic phase so obtained, meaning that it was possible to remove all the sodium chloride from the organic phase.

Next, to 100 ml of the organic phase containing EDA was added 20 ml of an aqueous solution containing 8.0 g of hydrochloric acid. The mixture was shaken for 10 minutes, the allowed to stand to effect separation, giving 23.2 ml of an aqueous phase. The results of the analysis showed that this aqueous phase contained all the EDA contained in the organic phase. The EDA concentration in the aqueous phase was 304 g/l.

EXAMPLE 14

To 100 ml of an aqueous ethylenediamine (EDA) hydrochloride solution containing 9.0 g of EDA, was added an equimolar amount of hydrochloric acid (HCl), 17.5 g of ammonia (NH₃), and 100 ml of an n-butanol mixed solution containing 33 ml of cyclohexanone. The mixture was shaken for 10 minutes, allowed to stand, then separate into an aqueous and an organic phases.

To 100 ml of the organic phase was then added 15 ml of an aqueous solution containing 9.0 g of sulfuric acid. The mixture was shaken for 10 minutes, allowed to stand, then separated to obtain 16.2 ml of an aqueous phase. This aqueous phase contained the entire amount of EDA contained in the organic phase. The EDA concentration in the aqueous phase was 330 g/l.

EXAMPLE 15

To 100 ml of an aqueous solution obtained by the reaction of ethylene dichloride (EDC) and an aqueous ammonia and having the following composition:

| | |
|---|---|
| EDA | 66 g/l |
| Diethylenetriamine (DETA) | 29 g/l |
| Triethylenetetramine (TETA) | 16 g/l |
| Tetraethylenepentamine (TEPA) | 6.4 g/l |
| Pentaethylenehexamine (PEHA) | 4.3 g/l |
| N—Aminoethylpiperazine (N—AEP) | 4.3 g/l |
| HCl | 117 g/l |
| NH$_3$ | 164 g/l | was added 100 ml of a 1:2 (by volume) mixed solvent of cyclohexanone and n-butanol. The mixture was shaken for 10 minutes, allowed to stand, then separated into aqueous and organic phases.

This gave 115 ml of an organic phase containing

| | |
|---|---|
| EDA | 38.4 g/l |
| DETA | 15.0 g/l |
| TETA | 7.6 g/l |
| TEPA | 3.1 g/l |
| PEHA | 1.9 g/l |
| N—AEP | 1.4 g/l |

The percentage extraction was 67% for EDA, 59% for DETA, 55% for TETA, 56% for TEPA, 51% for PEHA and 37% for N-AEP.

Next, to 80 ml of the organic phase was added 10 ml of water, then a water-saturated carbon dioxide gas was blown into the mixture at a rate of 100 ml/min for one hour. The mixture was then allowed to stand, and separated to obtain an aqueous phase containing 280 g/l of EDA, 110 g/l of DETA, 55 g/l of TETA, 23 g/l of TEPA, 14 g/l of PEHA and 10 g/l of N-AEP. The percent back-extraction of each amine was 100%.

EXAMPLE 16

To 200 ml of an aqueous solution containing 90 g/l of ethylenediamine (EDA) and 180 g/l of sodium chloride (NaCl) was added 200 ml of n-butanol containing 1.5 mole/l of Versatic Acid-10 having 10 carbon atoms (supplied by Shell Chemical). The mixture was shaken for 10 minutes, and then allowed to stand to effect phase separation, giving 263 ml of an organic phase containing 47.9 g/l of EDA.

Next, 15 ml of pure water was added to 180 ml of the organic phase. Water-saturated carbon dioxide gas was blown into the mixture at a rate of 100 ml/min for 2 hours. The mixture was than allowed to stand to effect phase separation, giving 21.5 ml of an aqueous EDA carbonate solution containing 320 g/l of EDA and 200 g/l of CO$_2$.

EXAMPLES 17 THROUGH 20

To 200 ml of an aqueous solution containing 18.0 g of each of the ethyleneamines listed in Table III and 36.0 g of sodium chloride (NaCl) was added 200 ml of a mixed solution of n-butanol containing 67 ml of cyclohexanone. The mixture was shaken for 10 minutes, allowed to stand, then separated into its aqueous and organic phases.

To 160 ml of the organic phase as obtained was then added 20 ml of pure water. The water-saturated carbon dioxide gas was then blown into the mixture at a rate of 100 ml/min for 2 hours and the ethyleneamine in the organic phase thereby back-extracted into the aqueous phase as a carbonate. The mixture was then allowed to stand and separated into aqueous and organic phases.

Next, 20 ml of the aqueous phase so obtained was charged into a 50 ml three-necked round-bottomed flask equipped with a condenser. The aqueous phase was then heated by a mantle heater to effect thermal decomposition of the ethyleneamine carbonate at the boiling point under total refluxing for 2 hours. The results are shown in Table III.

TABLE III

| | | Extraction | | | | Back-extraction | | | Thermal decomposition | | |
|---|---|---|---|---|---|---|---|---|---|---|---|
| | | Concentration of ethyleneamine upon extraction equilibrium | | Distribution coefficient (K) | % Extraction | Concentration of ethyleneamine in aq. phase (g/l) | Concentration of CO$_2$ in aq. phase (g/l) | % Back-extraction | Concentration of ethyleneamine (g/l) | Concentration of CO$_2$ (g/l) | % Decomposition |
| Example No. | Ethyleneamine | Org. phase (g/l) | Aq. phase (g/l) | | | | | | | | |
| 17 | Ethylenediamine (EDA) | 61.0 | 20.5 | 3.0 | 82.0 | 330 | 240 | 100 | 335 | 56 | 77 |
| 18 | Diethylenetriamine (DETA) | 57.2 | 26.7 | 2.1 | 76.3 | 310 | 135 | 100 | 315 | 27 | 80 |
| 19 | Triethylenetetramine (TETA) | 49.0 | 39.6 | 1.2 | 62.6 | 290 | 135 | 100 | 294 | 18 | 87 |
| 20 | Tetraethylenepentamine (TEPA) | 47.3 | 42.2 | 1.1 | 57.3 | 280 | 100 | 100 | 285 | 13 | 87 |

EXAMPLE 21

To 200 ml of an aqueous solution containing 106 g/l of triethylenetetramine (TETA) and 225 g/l of NaCl was added 200 ml of benzyl alcohol. The mixture was shaken for 10 minutes, allowed to stand, then separated to obtain 228 ml of an organic phase containing 55.2 g/l of TETA and 172 ml of an aqueous phase containing 50.1 g/l of TETA and 262 g/l of NaCl.

Next, 15 ml of pure water was added to 150 ml of the organic phase. Water-saturated carbon dioxide gas was blown into the mixture at a rate of 100 ml/min for 2 hours. The mixture was then allowed to stand and separated, thereby back-extracting all the TETA into an aqueous phase as a carbonate.

15 ml of the aqueous phase was thermally decomposed by the same procedures described in Examples 17 to 20 to obtain an aqueous solution containing 360 g/l of TETA and 18 g/l of CO$_2$.

EXAMPLE 22 THROUGH 25

The same procedures as described in Examples 17 to 20 were repeated respectively in these examples, except that the cyclohexanone used in Examples 17 to 20 was replaced with 200 ml of a mixed solution of n-butanol containing 67 ml of cyclopentanone. Results similar to those in Examples 17 to 20, respectively, were obtained.

EXAMPLE 26

To an aqueous reaction mixture obtained by the reaction of ethylene dichloride (EDC) and an aqueous ammonia was added a 50% calcium hydroxide cake giving an aqueous solution containing 65 g/l of ethylenediamine (EDA), 28 g/l of diethylenetriamine (DETA), 16 g/l of triethylenetetramine (TETA), 6.0 g/l of tetraethylenepentamine (TEPA), 4.0 g/l of pentaethylenehexamine (PEHA), 4.0 g/l of N-amino-ethylpiperazine (N-AEP), 176 g/l of $CaCl_2$ and 108 g/l of $NH_3$. To 200 ml of said aqueous solution was added 200 ml of a mixed solution of n-butanol containing 67 ml of cyclohexanone. The mixture was shaken for 10 minutes, allowed to stand, then separated to obtain 230 ml of an organic phase containing 46 g/l of EDA, 17 g/l of DETA, 9.2 g/l of TETA, 3.0 g/l of TEPA, 2.1 g/l of PEHA, and 1.8 g/l of N-AEP.

Next, 30 ml of pure water was added to 200 ml of the organic phase. Water-saturated carbon dioxide gas was blown into the mixture at a rate of 100 ml/min for 2 hours, following which the mixture was allowed to stand, then separated, thereby back-extracting all the ethyleneamines contained in the organic phase into an aqueous phase as carbonates.

20 ml of the aqueous phase was thermally decomposed by the same procedures as described in Examples 17 to 20 to obtain an aqueous solution containing 204 g/l of EDA, 75 g/l of DETA, 41 g/l of TETA, 13 g/l of TEPA, 9.3 g/l of PEHA, 8.0 g/l of N-AEP, and 50 g/l of $CO_2$.

EXAMPLE 27

To 10 ml of the aqueous solution obtained by thermal decomposition in Example 17, and containing 335 g/l of ethylenediamine (EDA) and 56 g/l of $CO_2$, was added 4.7 ml of an aqueous solution containing 240 g/l of NaOH. The mixture was shaken for 10 minutes, allowed to stand, then separated to obtain 10.8 ml of an aqueous solution containing 310 g/l of EDA and almost no $CO_2$ and 3.9 ml of an aqueous solution containing 350 g/l of $Na_2CO_3$ and almost no EDA.

EXAMPLE 28

To 15 ml of a back-extract (containing 320 g/l of ethylenediamine (EDA) and 235 g/l of $CO_2$) obtained by a procedure similar to that described in Example 17 was added 15 ml of n-butanol. Thermal decomposition was then effected by the same procedures as described in Example 17 to obtain an aqueous solution containing 325 g/l of EDA and 10 g/l of $CO_2$.

EXAMPLE 29

To 100 ml of an aqueous solution containing 4.45 g of ethylenediamine (EDA) and 17.5 g of $CaCl_2$ was added 100 ml of a mixed solution of n-butanol containing 33 ml of benzaldehyde. The mixture was shaken for 10 minutes, then allowed to stand to effect phase separation. As a result, 107 ml of an organic phase containing 38.6 g/l of EDA and 0.74 g/l of $CaCl_2$ and 93 ml of an aqueous phase containing 1.8 g/l of EDA and 187 g/l of $CaCl_2$ were obtained. The percentage extraction for EDA was 92.8% and the percentage extraction for $CaCl_2$ was 0.5%.

Next, 5 ml of pure water was added to 80 ml of the organic phase. Water-saturated carbon dioxide gas was blown into the mixture at a rate of 100 ml/min for 30 minutes to effect back-extraction of EDA from the organic phase in the form of the carbonate into the aqueous phase. The mixture was allowed to stand still to effect phase separation, giving 7 ml of an aqueous phase containing 210 g/l of EDA and 160 g/l of $CO_2$.

We claim:

1. In a process for selectively extracting an ethyleneamine with an extractant from an aqueous solution containing the ethyleneamine into an organic phase, followed by recovery of the ethyleneamine from the organic phase, the improvement comprising:
   (a) selectively extracting said ethyleneamine with an organic solvent extractant selected from the group consisting of alicyclic ketones, aldehydes and mixtures of at least one of these organic solvents with one or more other organic solvents; and
   (b) recovering said ethyleneamine from said organic phase by incorporating an aqueous carbonic acid solution or carbon dioxide gas in the organic phase containing the ethyleneamine extracted therein, thereby back-extracting the ethyleneamine in the form of a salt in an aqueous phase.

2. The process according to claim 1 wherein said extractant is at least one organic solvent selected from the group consisting of alicyclic ketones and mixtures thereof with other organic solvents.

3. The process according to claim 1 wherein said aqueous ethyleneamine-containing solution is a solution produced by the reaction between ethylene dichloride and an aqueous ammonia and containing ethyleneamine hydrochlorides, ammonium chloride and free ammonia.

4. The process according to claim 1 wherein said aqueous ethyleneamine-containing solution is a solution which has been obtained by incorporating an alkali in a solution produced by the reaction between ethylenedichloride and an aqueous ammonia and containing ethyleneamine hydrochlorides, ammonium chloride and free ammonia.

5. The process according to claim 1 wherein said organic solvent used as the extractant is a mixed solvent composed of a first organic solvent selected from the group consisting of ketones and aldehydes, and a second organic solvent selected from the group consisting of alcohols, ethers and esters.

6. The process according to claim 5 wherein the mixing ratio by volume of the first organic solvent to the second organic solvent is in the range of from 100:0 to 1:19

7. The process according to claim 5 wherein said second organic solvent is an alcohol having 3 to 8 carbon atoms.

8. The process according to claim 7 wherein said alcohol having 3 to 8 carbon atoms is butanol.

9. The process according to claim 1 wherein said alicylic ketone has a 5- or 6- membered ring.

10. The process according to claim 1 wherein said organic solvent is cyclohexanone methylcyclohexanone or cyclopentanone.

11. The process according to claim 1 wherein said organic solvent is an aliphatic aldehyde having 3 to 8 carbon atoms or an aromatic aldehyde.

12. The process according to claim 1 wherein said organic solvent is benzaldehyde.

13. The process according to claim 1 wherein said organic solvent is selected from the group consisting of alicyclic ketones and aldehydes, and the amount of said organic solvent is at least one mole per mole of the ethyleneamine present in the aqueous solution thereof.

14. The process according to claim 1 wherein said organic solvent used as the extractant is a mixed solvent composed of benzyl alcohol and an alicyclic ketone.

15. The process according to claim 1 wherein said extraction of the ethyleneamine is carried out in the presence of ammonia.

16. The process according to claim 15 wherein the amount of ammonia is at least equivalent to the total amount of the hydrochloric acid and calcium ion present in the aqueous ethyleneamine solution.

17. The process according to claim 1 wherein the amount of said carbonic acid or carbon dioxide is in the range of from 0.5 to 2 moles per mole of the ethyleneamine present in the organic phase.

18. The process according to claim 1 wherein the aqueous phase containing the ethyleneamine salt back-extracted therein is heated thereby to decompose the ethyleneamine salt for the recovery of free ethyleneamine.

* * * * *